United States Patent [19]

Winner

[11] 4,422,073
[45] Dec. 20, 1983

[54] COMBUSTIBLE GAS DETECTION SYSTEM

[75] Inventor: Joe K. Winner, Pinellas, Fla.

[73] Assignee: The Bendix Corporation, Southfield, Mich.

[21] Appl. No.: 315,684

[22] Filed: Oct. 27, 1981

[51] Int. Cl.³ .......... G08C 19/16; G08C 19/36
[52] U.S. Cl. .......... 340/870.21; 340/870.18; 340/870.29; 340/310 R; 340/632
[58] Field of Search ......... 340/870.26, 870.18, 340/870.28, 870.29, 870.39, 870.21, 632, 310 R, 310 A; 455/615, 617, 618

[56] References Cited

U.S. PATENT DOCUMENTS

| | | | |
|---|---|---|---|
| 3,467,889 | 9/1969 | Brough-Cunningham et al. | 340/870.18 |
| 3,793,636 | 2/1974 | Clark et al. | 340/870.28 |
| 4,077,030 | 2/1978 | Helava | 340/870.39 |
| 4,132,981 | 1/1979 | White | 340/870.05 |
| 4,236,144 | 11/1980 | Sunagawa | 340/870.18 |
| 4,328,494 | 5/1982 | Goodall | 340/870.18 |
| 4,350,980 | 9/1982 | Ward | 340/870.29 |

Primary Examiner—James J. Groody
Attorney, Agent, or Firm—Bruce L. Lamb; W. G. Christoforo

[57] ABSTRACT

A combustible gas detection system in which analog signals produced by a remotely located combustible gas sensor are converted to digital signals at the sensor and the digital signals control a coherent frequency shift keying modulator which impresses alternating signal currents, through an optically coupled isolator on a transmission line connecting the sensor with a control station. The transmission line is a two wire link of ordinary quality which carries power from the controller to the sensor as well as signals from the sensor to the controller.

1 Claim, 1 Drawing Figure

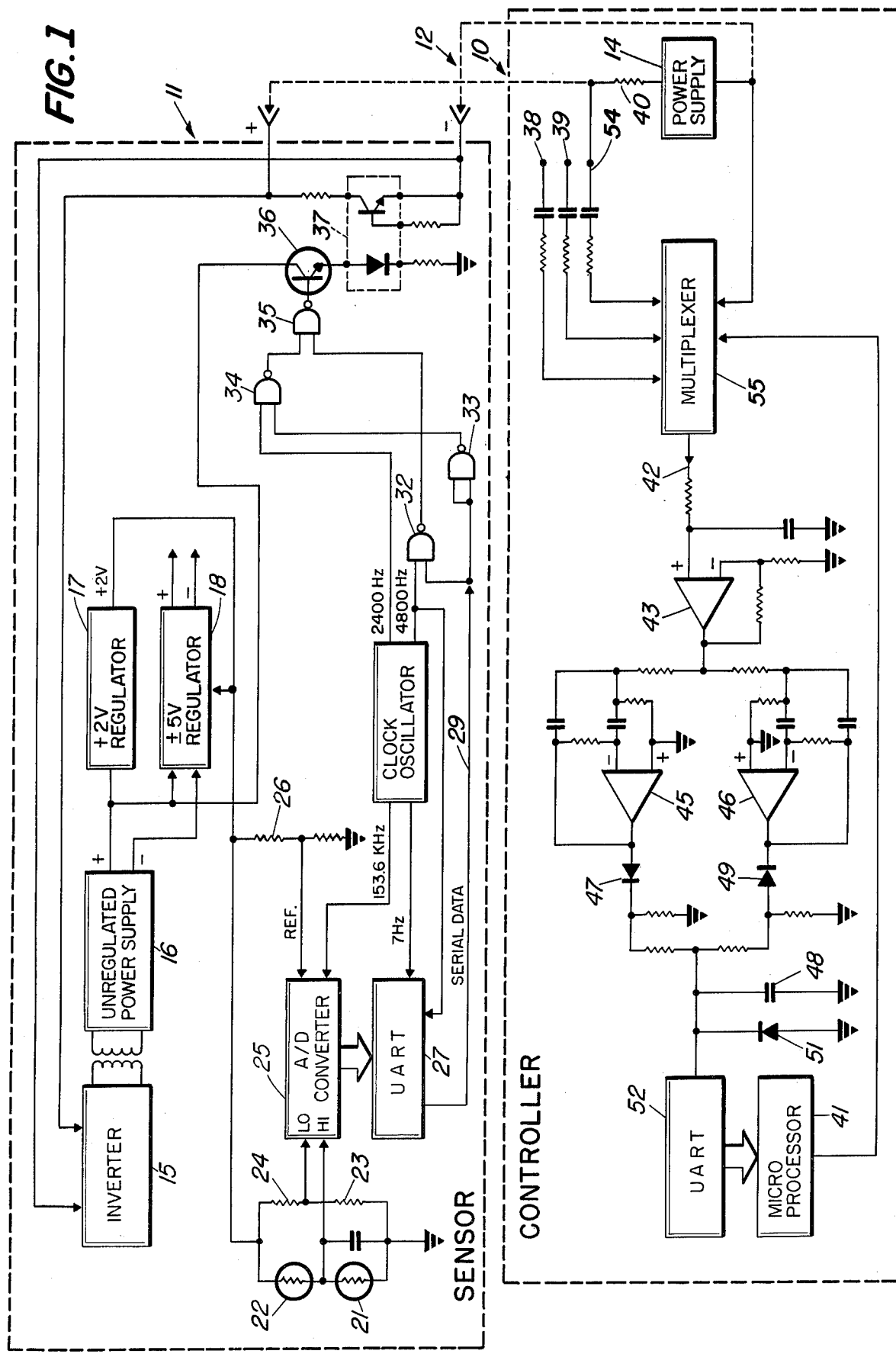

COMBUSTIBLE GAS DETECTION SYSTEM

The present invention relates to combustible gas detection systems. More particularly it relates to a combustible gas detection system having a combustible gas sensor remotely located from a control station and having a noise immune transmission system for communicating signals from the sensor to the control station.

Combustible gas detection systems with remotely located sensors are commonly used in large chemical processing plants in which operations are controlled from a central location. The combustible gas sensors in widest use are of the type described in U.S. Pat. No. 3,092,799 issued June 4, 1963 to A. R. Baker for "Apparatus for Detecting Combustible Gases Having an Electrically Conductive Member in a Refractory Material". Such sensors comprise a filament of resistance wire encapsulated in a refractory material which has been rendered catalytically active. A heating current is passed through the filament to maintain the temperature sensor at an elevated level. In the presence of a combustible gas the temperature level of the sensor becomes further elevated because of the catalytic combustion of the gas occurring at the refractory surface. Such a temperature increase causes a change in the resistance of the filament and a consequent change in the filament current. To distinguish current changes produced by a combustible gas from those which might result from a change in ambient temperature or from a change in the power supply voltage, the catalytically active sensor is connected, together with a similarly constructed filament which has not been catalytically activated, in a Wheatstone bridge circuit. The changes in current which occur at the bridge balance points will then be due to the presence of combustible gas alone, neglecting any long term changes in component values.

Conventionally, the direct current signal existing at the balance points of the sensor bridge is conducted without modification to the control station where the value of the signal is measured and interpreted in terms of combustible gas concentration. Typical values for such signals are in the range of 4–20 ma, depending upon the particular gas being sensed. Obviously when such low level signals are conducted for distances of several thousand feet, special care must be taken in the selection and installation of the transmission line to minimize noise. Moreover, apart from the likelihood of noise appearing on the line, the line characteristics directly affect the signal so that painstaking calibration procedures must be followed upon installation and periodically thereafter for each sensor of the system to insure that accurate signals are received at the control station.

It is an object of the invention to provide a combustible gas detection system having one or more remotely located sensors in which noise-free signals are transmitted from the sensors to a central control station.

It is another object of the invention to provide a combustible gas detection system having remotely located sensors in which common quality wire may be used to link the sensors with a central control station.

It is a further object of the invention to provide a combustible gas detection system having remotely located sensors in which highly accurate signals may be transmitted from the sensors to a central control station without necessity of calibrating the sensor-transmission line combination.

Other objects of the invention will become evident as an understanding thereof is gained through study of the following complete description and accompanying drawing.

Briefly, the invention comprises a combustible gas detection system in which a central control station designed to process digitally gas sensor data furnishes operating power over a common quality two wire link to one or more remotely located gas sensors. The gas sensors are of the catalytically active filament type which produce a comparatively low level analog signal output indicative of the concentration of combustible gas at the sensor location. The analog output signal of each sensor of the system is converted locally to a digital signal and the digital signal is transmitted to the control station by means of a coherent frequency shift keying system, over the same two wire link as supplies operating power to the sensor.

In the drawing:

The single FIGURE of the drawing is a functional block diagram of the invention showing the central controller and the elements of the data receiving and processing system sited thereat and a remotely located gas sensor module showing the elements of the data processing and transmission system contained therein.

Referring to the drawing, a centrally located controller 10 is shown linked to a remotely located sensor module 11 by a two wire transmission line 12 which may be several thousand feet in length. A power supply 14 at the controller furnishes 24 vdc power to sensor module 11 through transmission line 12. In the sensor module an inverter 15, which may suitably comprise a freerunning multivibrator, converts the dc input from line 12 to ac for transformation to a lower voltage, suitably 10 vac. The ac output of converter 15 is rectified in an unregulated power supply 16, the output of which is regulated to +2 V in regulator 17 and to ±5 V in bipolar regulator 18. Regulator 17 furnishes power to a sensor bridge comprising a catalytically active filamentary resistor 21 and a reference filamentary resistor 22 connected in series and connected in parallel with series connected resistors 23 and 24. The 5 V regulator 18 powers the integrated circuits of sensor module 11. The bridge balance point at the junction of sensor resistors 21 and 22 is connected to the high input of a 12 bit binary analog/digital converter 25. The bridge balance point at the junction of resistors 23 and 24 is connected to the low input of converter 25. Converter 25 may suitably be type ICL 7109 manufactured by Intersil Inc., Cupertino, Calif. In a converter of this type the voltage difference existing between the high and low inputs is integrated for a fixed time period. The integrated voltage is then deintegrated at a constant rate and the time required for the integrated voltage to return to zero is counted digitally. The digital count is then proportional to the magnitude of the analog voltage input. The reference voltage necessary for the operation of converter 25 is provided by a voltage divider 26 connected between +2 V and ground.

The analog signal from the sensor bridge, after conversion, is present in converter 25 as a 12 bit parallel format digital word. To permit transmission of the 12 bit word over a two wire transmission line the word is converted from parallel to serial format in a Universal Asynchronous Receiver Transmitter (UART) 27.

A clock oscillator 28 provides phase coherent, harmonically related clock signals at frequencies of 153.6 kHz, 4800 Hz, 2400 Hz and approximately 7 Hz. The 153.6 kHz clock signal is utilized by converter 25. The 4800 Hz signal serves as the transmitter clock for UART 27. The 4800 Hz also serves as the carrier for logic "1" bits when modulated onto transmission line 12. The 2400 Hz signal is the carrier for logic "0" bits. The 7 Hz signal operates with handshake logic connecting converter 25 and UART 27 to provide sampling and conversion of the analog signal at the rate of seven per second. Serial data from UART 27 appears on line 29 at a rate of 300 Baud. The data is applied to a frequency shift keying circuit 31 comprising NAND gates 32-35, transistor 36 and optically coupled isolator 37. A logic "1" level signal on line 29 enables gate 32 to pass 4800 Hz carrier to gate 35. At the same time, gate 33 inverts the "1" signal, disabling gate 34 causing that gate to produce a high output which enables gate 35 to pass 4800 Hz carrier to the base of transistor 36. A logic "0" level on line 29 disables gate 32, blocking transmission of 4800 Hz carrier and, after inversion in gate 33, enables gate 34 to pass 2400 Hz carrier to gate 35. Gate 32, being disabled by the "0" input, produces a high output enabling gate 35 to pass the 2400 Hz carrier to transistor 36.

Transistor 36 drives isolator 37, suitably type 4N36, consisting of a light emitting diode and a phototransistor. Light from the diode fluctuates at the 2400 or 4800 Hz carrier frequency, thereby rendering the phototransistor conductive at the same frequency, impressing a current modulation signal of about 20 ma on line 12.

At the controller 10, the current modulation signal on line 12 develops an alternating voltage across resistor 40 which is decoupled from d.c. through network 54 as one channel input to a multiplexer 55. Sensor modules similar to sensor module 11 may be coupled to other channel inputs of multiplexer 55 through networks 38, 39 and resistors corresponding to resistor 40. Multiplexer 55 switches channels under command of a microprocessor 41 to connect a particular sensor input channel to the output 42 thereof. Signals from multiplexer 55 are filtered to remove high frequency noise and amplified in amplifier 43, the output of which is connected in parallel to operational amplifiers 45 and 46. The feedback network of amplifier 45 is designed to provide a bandpass characteristic with a center frequency of 4800 Hz and a Q of about 10. The feedback network of amplifier 46 is designed to provide a bandpass characteristic with a center frequency of 2400 Hz and a Q of about 4 so that the times required for the amplifiers to stabilize after a shift in carrier frequency are approximately equal. The output of amplifier 45 is rectified in a diode 47 poled to charge a storage capacitor 48 positively. Output of amplifier 46 is rectified in a diode 49 poled to discharge capacitor 48 to ground level. Diode 51 ensures that capacitor 48 will not become negatively charged.

The data which appears on capacitor 48 serially is stored in the receiver register of a UART 52, then transferred in parallel format to microprocessor 41. Microprocessor 41 interprets the received data in terms of the percentage of Lower Explosive Limit of the combustible gas being sensed and provides an output indication of the same and actuates an alarm or adjusts process controls in response thereto, as may be desired.

The conversion of low level analog signals to high level digital signals transmitted by frequency shift keying of carrier signals at frequencies which are well removed from the 60 Hz at which most line induction noise occurs renders the system substantially immune to interference. Accuracy is improved by the high degree of resolution with which analog to digital conversion is accomplished and by the fact that the signal level of the transmitted signals is not dependent upon the magnitude of the sensor signal. By employing phase coherent 4800 Hz and 2400 Hz both as the UART clock and as carriers for the data signals, data signals are received and detected at the control station with minimum distortion.

The invention claimed is:

1. In a combustible gas detection system having a central control station and a remotely located combustible gas sensor of the catalytically activated resistance bridge type providing an analog signal indicative of the concentration of combustible gas at the sensor location, a noise immune transmission system for transmitting signals from said sensor to said control station, comprising a two-wire transmission line connecting said control station with said sensor location, means supplying d.c. power to said transmission line;

means at said sensor location for converting d.c. power received from said transmission line to a.c. power;

means for converting said a.c. power to regulated d.c. operating power for said sensor;

an analog to digital converter at said sensor location for converting said analog signal from said sensor into a parallel format binary digital signal;

means for converting said parallel format digital signal into a serial format digital signal;

a clock oscillator at said sensor providing at least a pair of harmonically related, phase coherent clock signals of different frequency;

keying means controlled by said serial format digital signal for selecting one of said clock signals upon the appearance of a logic "1" in said serial digital signal and for selecting the other of said clock signals upon the appearance of a logic "0" in said serial digital signal; and an optically coupled isolator for applying said clock signal selected by said keying means to said transmission line, said isolator including a light emitting diode to which said clock signal selected by said keying means is applied, a load resistor, and a phototransistor connected through said load resistor to said transmission line, said phototransistor responding to light emitted by said light emitting diode to vary current through said load resistor.

* * * * *